US006228377B1

United States Patent
Sebillotte-Arnaud

(10) Patent No.: US 6,228,377 B1
(45) Date of Patent: *May 8, 2001

(54) WATER-IN-OIL EMULSION CONTAINING FUSED SILICA AND A POLYSACCHARIDE ALKYL ETHER

(75) Inventor: Laurence Sebillotte-Arnaud, L'Hay les Roses (FR)

(73) Assignee: L'oreal, Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/141,332

(22) Filed: Aug. 27, 1998

(30) Foreign Application Priority Data

Aug. 28, 1997 (FR) .................................................. 97 10756

(51) Int. Cl.[7] .............................. A61K 7/00; A61K 7/021; A61K 7/025; A61K 7/06; A61K 7/11
(52) U.S. Cl. .............................. 424/401; 424/63; 424/64; 424/70.1; 424/70.7; 424/70.13; 514/844; 514/845; 514/846; 514/938
(58) Field of Search .......................... 514/938; 424/401, 424/70.12, 70.13, 70.7

(56) References Cited

U.S. PATENT DOCUMENTS 5,489,429  2/1996  Griat et al. .
5,582,832 * 12/1996  Pillai et al. .
5,833,967 * 11/1998  Ramin .................................. 424/70.4

FOREIGN PATENT DOCUMENTS

| 0 281 360 | 9/1988 | (EP) . |
| 0708114 * | 4/1996 | (EP) . |
| 0 708 114 A1 | 4/1996 | (EP) . |
| 0 795 321 A1 | 9/1997 | (EP) . |
| 0 795 322 A1 | 9/1997 | (EP) . |

OTHER PUBLICATIONS

Majewicz, Thomas G. and Modi, Jashawant J., Research disclosure of "Oil–based cosmetic and therapeutic compositions containing ethylguar," 10/1995.*
Hawley, Gessner G., The Condensed Chemical Dictionary 10th Ed., Van Nostrand Reinhold Co., New York, pp 887 and 920, 1981.*
Wenninger John A., and McEwen G. N., Jr., International Cosmetic Ingredient Dictionary and Handbook 7th Ed., The Cosmetic, Toiletry and Fragrance Association, Washington, DC, pp. 1246, 1997.*

* cited by examiner

Primary Examiner—Diana Dudash
Assistant Examiner—Alysia Berman
(74) Attorney, Agent, or Firm—Oblon, Spivak, McClelland, Maier & Neustadt, P.C.

(57) ABSTRACT

A water-in-oil emulsion is provided having a liquid fatty phase and an aqueous phase, wherein the liquid fatty phase contains a fumed silica and at least one polysaccharide alkyl ether formed of units containing at least two different saccharide rings, each unit containing at least one hydroxyl group substituted with a hydrocarbon-based chain, and from 0% to 5% by weight, relative to the total weight of the emulsion, of at least one emulsifying surfactant, and the liquid fatty phase contains at least one medium which is a solvent for the polysaccharide alkyl ether, that is useful in particular in the cosmetics and/or dermatological fields.

19 Claims, No Drawings

WATER-IN-OIL EMULSION CONTAINING FUSED SILICA AND A POLYSACCHARIDE ALKYL ETHER

BACKGROUND OF THE INVENTION

1. Field of the Invention

The present invention relates to a water-in-oil emulsion and its use in the cosmetics, dermatological, veterinary and/or agrifood fields, particularly in the form of a white or colored cream to care for, make up, remove make-up from, and/or provide antisun protection to human skin and/or mucous membranes, as well as to prepare a cream for the treatment of skin diseases and/or mucous membrane diseases.

2. Discussion of the Background

In the cosmetics field, it is common to use creams consisting of a water-in-oil (W/O) emulsion containing an aqueous phase dispersed in a liquid fatty phase (generally referred to as the oily phase). These emulsions contain an oily continuous phase and thus allow a lipid film to be formed on the surface of the skin to prevent transepidermal water loss and protect the skin against external attack. The emulsions are particularly suitable for protecting and nourishing the skin, and in particular for treating dry skin.

These emulsions frequently have stability problems, making them difficult to manufacture. Various means have been proposed to overcome this drawback. One known means consists of incorporating into the emulsion a large amount of emulsifying surfactant, which can be up to 10% by weight relative to the total weight of the emulsion. However, it is known that emulsifiers used in large amounts can be irritating towards certain types of skin. Moreover, the creams obtained are often compact and heavy. In addition, the surfactants need to be chosen as a function of the polarity of the oils and are thus only compatible with a limited number of oils, limiting the variety of the formulations.

SUMMARY OF THE PRESENT INVENTION

Accordingly, one object of the present invention is to provide a water-in-oil emulsion which does not have the above mentioned drawbacks and which contains a reduced amount of emulsifying surfactant.

Thus, the Applicant has found, surprisingly, that it is possible to obtain a water-in-oil emulsion having good cosmetic properties and good stability by using a specific combination of thickener for the oily phase.

DETAILED DESCRIPTION OF THE PREFERRED EMBODIMENTS

The present invention relates to a water-in-oil emulsion containing a liquid fatty phase, wherein the liquid fatty phase contains at least fumed silica and at least one polysaccharide alkyl ether formed of units containing at least two different saccharide rings, wherein each unit of the polysaccharide alkyl ether contains at least one hydroxyl group substituted with a saturated hydrocarbon-based alkyl chain, and from 0% to 5% by weight, relative to the total weight of the emulsion, of at least one emulsifying surfactant, wherein the liquid fatty phase contains at least one medium which is a solvent for the polysaccharide alkyl ether.

Due to the combination of fumed silica and polysaccharide alkyl ether, the emulsion according to the present invention is stable despite the low amount, or even absence, of emulsifying surfactant. In the present invention composition, the aqueous phase preferably disperses perfectly in the liquid fatty phase. The emulsion obtained is easy to apply to the skin or to mucous membranes and gives a soft, fresh and comfortable sensation when applied.

Depending on the percentage of thickener used, an emulsion of more or less fluid texture can be obtained. The expression "emulsion of fluid texture" is understood to mean an emulsion which flows under its own weight and has a viscosity of from about 2 to 15 poises, i.e. from 0.2 to 1.5 Pa.s. Conventional emulsions have a viscosity of about 20 to 80 poises, i.e. from 2 to 8 Pa.s. The emulsion according to the present invention has the advantage of being able to be fluid, creamy and comfortable while at the same time having good stability for one month at room temperature.

By comparison with the emulsion according to the present invention, it has been observed that an emulsion which is similar but comprises only one thickener (fumed silica or polysaccharide alkyl ether) has a coarser and less stable dispersed aqueous phase than the emulsion of the present invention.

The addition of polysaccharide alkyl ether makes it possible to reduce the coarse appearance of an emulsion whose oily phase is thickened with fumed silica alone.

Thus, another subject of the invention is the use of a polysaccharide alkyl ether formed of units containing at least two different saccharide rings, each unit containing at least one hydroxyl group substituted with a hydrocarbon-based chain and fumed silica, to stabilize a water-in-oil emulsion.

In the thickener combined with the fumed silica according to the invention, the term "hydrocarbon-based chain" is understood to refer to a linear or branched chain containing from 1 to 24, preferably from 1 to 10, better still from 1 to 6 and more especially from 1 to 3, carbon atoms optionally containing from 1 to 4 C=C bonds. Preferably, the hydrocarbon based chain includes methyl, ethyl, ethenyl, n-propyl, propenyl, isopropyl, n-butyl, isobutyl, tert-butyl and n-pentyl. These alkyl ethers can be manufactured as described in documents EP-A-281.360 and EP-A 708,114, the contents of which are hereby incorporated by reference.

According to a preferred embodiment of the invention, the polysaccharide alkyl ether has a weight-average molecular weight of greater than 100,000, and preferably greater than 200,000. This molecular weight can preferably be up to 1 million. This alkyl ether can contain from 1 to 6, and better still from 2 to 4, hydroxyl groups per unit, substituted with a saturated or unsaturated hydrocarbon-based chain.

The saccharide rings are preferably chosen from mannose, galactose, glucose, faranose, rhamnose and arabinose.

According to a preferred embodiment of the invention, the polysaccharide alkyl ether is an alkyl ether of a gum, and more preferably of a gum which is nonionic overall, i.e. one which contains few or no ionic groups. As appropriate gums, mention may be made, for example, of guar gum, in which the unit comprises a galactose and a mannose, carob gum, in which the unit comprises a galactose and a mannose, karaya gum, which is a complex mixture of rhamnose, galactose and galacturonic acid, and gum tragacanth, which is a complex mixture of arabinose, galactose and galacturonic acid.

According to a preferred embodiment of the invention, the polysaccharide alkyl ether is a guar gum derivative. Thus, preferably, the alkyl ether is an alkyl galactomannan with a $C_1$ to $C_6$, and better still $C_1$ to $C_3$, alkyl chain and more preferably ethyl guar having a degree of substitution of from 2 to 3, and most preferably from about 2.5 to 2.8, as described in the documents RD 95378007 (October 1995) and EP-A-708,114. This gum is sold in particular by the company Aqualon under the names N-Hance-AG 200® and N-Hance AG 50®.

Advantageously, the polysaccharide alkyl ether can be present in an amount such that the ratio (by weight) of the amount of oil to the amount of polysaccharide alkyl ether is chosen in the range from 5 to 1000.

Preferably, the polysaccharide alkyl ether is present in the liquid fatty phase of the emulsion at an active material concentration ranging from 0.1 to 16% by weight relative to the total weight of the emulsion, and more preferably from 0.2 to 5% by weight.

The fumed silica which can be used in the composition according to the present invention is preferably a fumed silica, which can be in the form of hydrophilic fumed silica or hydrophobic fumed silica.

The fumed silicas can be obtained, for example, by high-temperature hydrolysis of a volatile silicon compound in an oxyhydrogen flame, producing a fmely divided silica. This process makes it possible in particular to obtain hydrophilic silicas which have a large number of silanol groups at their surface. Such hydrophilic silicas are sold, for example, under the tradenames "Aerosil 130®", "Aerosil 200®", "Aerosil 255®", "Aerosil 300®", "Aerosil 380®" by the company Degussa and "CAB-O-SIL HS-5®", "CAB-O-SIL EH-5®", "CABO-SIL LM-130®", "CAB-O-SIL MS-55®", "CAB-O-SIL M-5®" by the company Cabot.

It is possible to chemically modify the surface of the fumed silica by chemical reaction, generating a decrease in the number of silanol groups. In particular, silanol groups can be substituted with hydrophobic groups to obtain a hydrophobic silica.

The hydrophobic groups can be:
trimethylsiloxy groups, which are obtained in particular by treatment of fumed silica in the presence of hexamethyldisilazane. Silicas thus treated are known as "silica silylate" according to the CTFA (6th edition, 1995). They are sold, for example, under the references "Aerosil R812®" by the company Degussa and "CAB-OSIL TS-530®" by the company Cabot;
dimethylsilyloxy or polydimethylsiloxane groups, which are obtained in particular by treatment of fumed silica in the presence of polydimethylsiloxane or dimethyldichlorosilane. Silicas thus treated are known as "silica dimethyl silylate" according to the CTFA (6th edition, 1995). They are sold, for example, under the references "Aerosil R972®", "Aerosil R974®" by the company Degussa, "CAB-O-SIL TS-610®" and "CAB-O-SIL TS-720®", by the company Cabot.

The fumed silica preferably has a particle size which can be nanometric to micrometric, more preferably ranging approximately from 5 to 200 nm, most preferably from 20 to 100 nm.

The emulsion according to the present invention can comprise fumed silica in an amount ranging from 0.5% to 25% by weight, preferably from 1 to 20% by weight, even more preferably from 1 to 10%, relative to the total weight of the emulsion. The liquid fatty phase of the emulsion according to the present invention comprises at least one medium which is a solvent for the polysaccharide alkyl ether, which can be an oil. In other words, the polysaccharide alkyl ether is a thickener for the oils. The term "oil" is understood to refer to any fatty material which is liquid at room temperature.

Among the oils which can be used as solvent medium for the polysaccharide alkyl ether according to the invention, mention may be made of:

oils of plant origin, such as liquid triglycerides, including, but not limited to, sunflower oil, corn oil, soybean oil, jojoba oil, marrow oil, grapeseed oil, sesame oil, hazelnut oil, apricot oil, macadamia oil and castor oil; caprylic/capric acid triglycerides such as those sold by the company Stearineries Dubois or those sold under the names Miglyol 810, 812 and 818® by the company Dynamit Nobel;

oils of animal origin, such as lanolin;

oils of mineral origin;

synthetic oils, including fatty alcohols such as 2-octyldodecanol; esters, and in particular fatty acid esters, preferably esters having a total number of carbon atoms chosen between 12 and 80 and more preferably between 16 and 50; phenylsilicones, preferably phenyltrimethicones, diphenyldimethicones and polymethylphenylsiloxanes.

A person skilled in the art will know, on the basis of his or her knowledge, how to determine, by simple routine tests, the oils which are solvents for the polysaccharide alkyl ether.

Complementary oils that are not solvents for the polysaccharide alkyl ether can also be added to the oily phase of the emulsion. Suitable complementary oils, include, but are not limited to, silicone gums and resins that are liquid at room temperature, partially fluorinated hydrocarbon-based oils, perfluoro oils, silicone oils free of aromatic groups, such as linear or branched polysiloxanes, including, but not limited to, polydimethylpolysiloxanes, polyethylmethylpolysiloxanes, polyalkylmethylsiloxanes and cyclic polysiloxanes such as octamethylcyclotetrasiloxane and decamethylcyclopentasiloxane or mixtures thereof, fluorosilicone oils; polysiloxanes functionalized with one or more hydroxyl functions and/or one or more polyether groups, such as dimethicone copolyols; and linear or branched hydrocarbons, such as liquid petroleum jelly, isohexadecane and isododecane.

The amount of oil which can be introduced into the emulsion can represent from 20% to 90% of the total weight of the emulsion.

The oils which are solvents for the polysaccharide alkyl ether can be present in a proportion of from 59 to 99.4% by weight, relative to the total weight of the oily phase of the composition, and preferably from 72% to 98.5%. The complementary oils can be added to the composition in an amount which can range from 0% to 75% by weight, relative to the total weight of the oily phase, and preferably from 0 to 50% by weight.

Waxes which are commonly used in cosmetic compositions can also be added to the oily phase. Suitable waxes include, but are not limited to, beeswax, microcrystalline wax, polyethylene waxes and silicone waxes. The waxes can be added in a content ranging from 0 to 20% by weight relative to the weight of the emulsion.

In the emulsion according to the present invention, the aqueous phase can be present in an amount ranging from 3% to 90% by weight, relative to the total weight of the emulsion, preferably from 3% to 70% by weight and more preferably from 10% to 50% by weight. The aqueous phase can also comprise aqueous gelling agents, such as the polyacrylic acids sold under the name "Carbopol°®" by the company Goodrich, or alternatively the poly(2-acrylamido-2-methylpropanesulphonic acid) polymers sold under the name "Hostacerin Amps®" by the company Hoechst.

In a known manner, the emulsion according to the present invention can contain a small amount of an emulsifying surfactant for a W/O emulsion. As emulsifiers which can be used in the present invention, mention may be made of fatty acid esters of glucose, such as methylglucose dioleate; fatty acid esters of glycerol, such as glyceryl isostearate, glyceryl oleate and glyceryl ricinoleate; fatty acid esters of sorbitol, such as sorbitan tristearate and sorbitan di- or trioleate; dimethicone copolyols, such as those sold under the name "Dow Coming 3225C®" by the company Dow Coming or under the name "Abil EM97®" by the company Goldschmidt; alkyldimethicone copolyol, and in particular cetyldimethicone copolyol, which is sold, for example, under the names "Abil WE09®" and "Abil EM90®" by the company Goldschmidt, and more generally any emulsifier having an HLB (hydrophilic lipophilic balance) of less than or equal to 6. The amount of emulsifier can represent from 0.1 to 3% and preferably from 0.1 to 2% of the total weight of the emulsion. Most preferably, the emulsion comprises no emulsifier for a W/O emulsion.

The emulsion according to the present invention is prepared according to conventional techniques known to those skilled in the art. For example, it can be prepared by dissolving the polysaccharide alkyl ether in the oily phase heated to 80–90° C, followed by adding the fumed silica to the mixture in order to obtain an oily gel. The aqueous phase is then added portion-wise and, after vigorous stirring, the water-in-oil emulsion is obtained.

For topical application, the composition according to the present invention must contain a physiologically acceptable medium, i.e. one which is compatible with human skin, mucous membranes and/or keratinic fibers such as hair.

The emulsion of the present invention can also contain conventional adjuvants that are common in the cosmetics and/or dermatological fields, such as active agents, preserving agents, antioxidants, completing agents, solvents, fragrances, fillers, screening agents, bactericides, odor absorbers, dyestuffs and lipid vesicles. The amounts of these various adjuvants are those used conventionally in the field considered and, for example, from 0.01 to 20% of the total weight of the emulsion depending on their nature. These adjuvants, when present, can be introduced into the fatty phase or into the aqueous phase. Their amount and their nature must be such that the stability of the emulsion is conserved.

The emulsion according to the present invention preferably has aqueous phase globules having a size which can range from 10 to 70 µm.

The present emulsion can also contain at least one cosmetic and/or dermatological active agent to care for and/or make up and/or remove make-up from and/or provide antisun protection to the skin and/or mucous membranes.

The emulsion according to the present invention finds its application in a large number of cosmetic and/or dermatological treatments for the skin, including the scalp, in particular to care for and/or make up (lipstick, eyeliner, foundation, mascara, concealers, eyeshadow or blusher) and/or remove make-up from and/or provide antisun protection to the skin, the hair, the eyelashes, the eyebrows, the nails or mucous membranes. It may be used also for the manufacture of a composition intended for the treatment of skin diseases and/or mucous membrane diseases.

Thus, the emulsion of the present invention can be used as defined above in a cosmetic composition for treating the skin, the hair, the eyelashes, the eyebrows, the nails and/or mucous membranes.

The present emulsion can also be used for the manufacture of a pharmaceutical and/or dermatological composition intended for the treatment of skin diseases and/or mucous membrane diseases.

The subject of the present invention is also a nontherapeutic cosmetic treatment process for the skin, the hair, the eyelashes, the eyebrows, the nails and/or mucous membranes, characterized in that an emulsion or a composition as defined above is applied to the skin, the hair, the eyelashes, the eyebrows, the nails or mucous membranes.

EXAMPLES

Having generally described this invention, a further understanding can be obtained by reference to certain specific examples which are provided herein for purposes of illustration only and are not intended to be limiting unless otherwise specified.

Examples 1 to 4

4 compositions according to the present invention are given below, compositions 1 and 2 having been actually prepared and compositions 3 and 4 being hypothetical examples:

| EXAMPLES | Example 1<br>Hair conditioner | Example 2<br>Care product<br>for around the eyes | Example 3<br>Body milk | Example 4<br>Hand cream |
|---|---|---|---|---|
| Silicon oil (1) | 55 | — | 38 | 50 |
| Capric/caprylic acid triglycerides | — | 55 | 39 | — |
| Ethyl guar with a degree of substitution of about 2.5 (2) | 0.36 | 0.36 | 0.36 | 0.36 |
| Hyderophobic fumed silica (3) | 4.7 | 4 | 2 | 3.5 |
| Preserving agent | qs | qs | qs | qs |
| Glycerol | — | — | — | 5 |
| Demineralized water | qs 100 | qs 100 | qs 100 | qs 100 |
| CHARACTERISTICS | Thick, white cream which feels very soft and fresh when applied. | Thick, white cream which feels very soft and fresh when applied. | White milk which feels very soft and fresh when applied. | Thick, white cream which feels very soft and fresh when applied. |

(1) sold under the name "Dow Corning 556 Cosmetic Fluid ®" by the company Dow Corning
(2) sold under the name "N-Hance AG 200 ®" by the company Aqualon
(3) sold under the name "Aerosil R-972 ®" by the company Degussa The amounts indicated are expressed in grams.

The compositions were prepared by dissolving the ethyl guar in the oily phase heated to 80–90° C., followed by adding fumed silica to the mixture in order to obtain an oily gel. Next, the aqueous phase was added portion-wise to the oily gel and, after stirring, a water-in-oil emulsion was obtained. It was observed that the emulsions were stable for at least one month at room temperature.

Obviously, numerous modifications and variations of the present invention are possible in light of the above teachings. It is therefore to be understood that within the scope of the appended claims, the invention may be practiced otherwise than as specifically described herein.

The application is based on French priority document 9710756, filed with the French Patent Office on Aug. 28, 1997, the entire contents of which are hereby incorporated by reference.

What is claimed is:

1. A water-in-oil emulsion comprising a liquid fatty phase and an aqueous phase, wherein the liquid fatty phase comprises fumed silica and at least one polysaccharide alkyl ether guar gum containing an ethyl chain with a degree of substitution of from 2 to 3 and from 0% to 5% by weight, relative to total weight of the emulsion, of at least one emulsifying surfactant, wherein the liquid fatty phase further comprises at least one medium which is a solvent for the polysaccharide alkyl ether.

2. The emulsion according to claim 1, wherein the polysaccharide alkyl ether has a weight-average molecular weight of greater than 200,000.

3. The emulsion according to claim 1, wherein the emulsion further comprises an oil and the polysaccharide alkyl ether is present in an amount such that the ratio, by weight of the amount of oil to the amount of polysaccharide alkyl ether is in the range from 5 to 1000.

4. The emulsion according to claim 1, wherein the polysaccharide alkyl ether is present in an amount ranging from 0.1 to 16% of the total weight of the emulsion.

5. The emulsion according to claim 4, wherein the polysaccharide alkyl ether is present in an amount ranging from 0.2 to 5% of the total weight of the emulsion.

6. The emulsion according to claim 1, wherein the fumed silica is a hydrophobic fumed silica.

7. The emulsion according to claim 1, wherein the fumed silica is present in an amount ranging from 0.5% to 25% by weight, relative to the total weight of the emulsion.

8. The emulsion according to claim 7, wherein the fumed silica is present in an amount ranging from 1% to 20% by weight, relative to the total weight of the emulsion.

9. The emulsion according to claim 1, wherein the liquid fatty phase represents from 20% to 90% of the total weight of the emulsion.

10. The emulsion according to claim 1, wherein the medium which is a solvent for the polysaccharide alkyl ether is present in an amount ranging from 59% to 99.4% by weight, relative to the total weight of the liquid fatty phase of the composition.

11. The emulsion according to claim 1, wherein the liquid fatty phase further comprises at least one complementary oil which is not a solvent for the polysaccharide alkyl ether.

12. The emulsion according to claim 11, wherein the complementary oil is present in an amount ranging from 0% to 75% by weight, relative to the total weight of the liquid fatty phase.

13. The emulsion according to claim 1, further comprising at least one active agent selected from the group consisting of cosmetic and dermatological active agents.

14. The emulsion according to claim 1, further comprising at least one ingredient selected from the group consisting of preserving agents, vitamins, fragrances, antioxidants, fillers, pigments, waxes, and mixtures thereof.

15. A cosmetic or dermatological composition, comprising an emulsion according to claim 1 and a cosmetically or dermatologically acceptable carrier.

16. A cosmetic treatment method comprising applying to a body part in need thereof an emulsion according to claim 1.

17. The cosmetic treatment method according to claim 16, wherein said body part in need thereof is a member selected from the group consisting of skin, hair, nails and mucous membranes.

18. The cosmetic treatment method according to claim 17, wherein said hair is a member selected from the group consisting of head hair, eyelashes and eyebrows.

19. A method for stabilizing water-in-oil emulsions, comprising combining with said emulsion a fumed silica and a polysaccharide alkyl ether guar gum containing an ethyl chain with a degree of substitution of from 2 to 3.

* * * * *

UNITED STATES PATENT AND TRADEMARK OFFICE
CERTIFICATE OF CORRECTION

PATENT NO.    : 6,228,377 B1
DATED         : May 8, 2001
INVENTOR(S)   : Laurence Sebillotte-Arnaud It is certified that error appears in the above-identified patent and that said Letters Patent is hereby corrected as shown below:

Column 7,
Line 50, "2 to 3" should read -- 2 to 3, --;
Line 61, "by weight" should read -- by weight, --.

Column 10,
Line 3, delete "polysaccharide alkyl ether".

Signed and Sealed this

Eleventh Day of June, 2002

*Attest:*

*Attesting Officer*

JAMES E. ROGAN
*Director of the United States Patent and Trademark Office*